United States Patent [19]

Hardt

[11] 4,116,968

[45] Sep. 26, 1978

[54] PROCESS FOR THE PRODUCTION OF 2-VINYL PYRIDINE

[75] Inventor: Peter Hardt, Visp, Switzerland

[73] Assignee: Lonza, Ltd., Basel, Switzerland

[21] Appl. No.: 851,786

[22] Filed: Nov. 15, 1977

[30] Foreign Application Priority Data

Nov. 15, 1976 [CH] Switzerland .................. 14339/76

[51] Int. Cl.$^2$ .................. C07D 213/06; C07D 213/38
[52] U.S. Cl. .................. 260/290 V; 260/293.69; 260/296 R
[58] Field of Search .................. 260/290 V, 296 R

[56] References Cited

U.S. PATENT DOCUMENTS

| 3,660,514 | 5/1972 | Cichowski | 260/290 V |
| 3,929,799 | 12/1975 | Thyret | 260/290 V |

FOREIGN PATENT DOCUMENTS

| 2,615,309 | 3/1977 | Fed. Rep. of Germany | 260/290 V |
| 850,114 | 9/1960 | United Kingdom | 250/290 V |

*Primary Examiner*—Alan L. Rotman
*Attorney, Agent, or Firm*—Fisher, Christen & Sabol

[57] ABSTRACT

A process for the production of 2-vinyl pyridine from a 2-(β-substituted ethyl)-pyridine involves using, as the starting material, a 2-(β-aminoethyl)-pyridine having the formula set out below. The 2-(β-aminoethyl)-pyridine is split by the action of a carrier-bound alkali hydroxide, as a catalyst, at a temperature between 100° and 500° C. into 2-vinyl pyridine and the corresponding secondary amine. The 2-(β-aminoethyl)-pyridine has the formula:

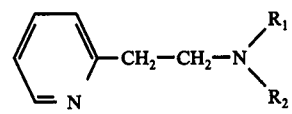

wherein $R_1$ is the same as or different from $R_2$, and $R_1$ and $R_2$ each are alkyl having one to eight carbon atoms, cycloalkyl, wherein the alkyl moiety has three to eight carbon atoms, or aralkyl, wherein the alkyl moiety has one to eight carbon atoms, or $R_1$ and $R_2$ together are $-(CH_2)_n-$ wherein $n$ is 4 or 5 or $R_1$ and $R_2$ together are $-(CH_2)_2-O-(CH_2)_2$.

8 Claims, No Drawings

PROCESS FOR THE PRODUCTION OF 2-VINYL PYRIDINE

BACKGROUND OF THIS INVENTION

1. Field of This Invention

This invention relates to a process for the production of 2-vinyl pyridine.

2. Prior Art

It is generally known that 2-vinyl pyridine can be produced in a two-step reaction from 2-picoline and formaldehyde by way of 2-(β-hydroxyethyl)-pyridine as the intermediate. For carrying out such reactions, numerous processes have been developed. The processes, among other things, differ in that the basic reactions were carried out by stages or in a single process step. A particular disadvantage of these processes is that, in order to guarantee a sufficiently selective reaction course in the first reaction step, 2-picoline must be used in an excess of 100 to 500 percent (see British Pat. No. 850,114 and West German Pat. No. 2,002,661).

With other production processes, which are based on catalytic dehydration of 2-ethyl pyridine, complete isolation of 2-vinyl pyridine is cumbersome and expensive because the boiling points of the educt and end product are very close (see *Ullmanns Encyclopedia of Technical Chemistry*, Third Edition, No. 18, 103).

In addition, it is also known to produce 2-vinyl pyridine from acrylonitrile and acetylene (see Swiss Patent Application No. 12139/75). In such case, the reaction takes place with the help of a catalyst which forms from cobaltocene. Unfortunately, cobaltocene or the catalyst which forms from it causes undesirable polymerization [see *Mem. Inst. and Ind. Res.*, Osaka Univ., Vol. 28, 113, (1971)]. As a result, 2-vinyl pyridine is obtained only in a yield of 34.4 percent.

BROAD DESCRIPTION OF THIS INVENTION

An object of this invention is to provide a process for the production of 2-vinyl pyridine from an easily accessible 2-(β-substituted ethyl)-pyridine. More specifically, an object of this invention is to provide a process for the production of 2-vinyl pyridine from an easily obtainable 2-(β-aminoethyl)-pyridine.

Other advantages and objects of this invention are set out herein or are obvious herefrom to one ordinarily skilled in the art.

The advantages and objects of this invention are achieved by the process of this invention.

It has been found that, in the case of a process for the production of 2-vinyl pyridine from a 2-(β-aminoethyl)-pyridine of the formula, set forth below, all the above-mentioned disadvantages of the prior art processes are avoided.

The process of this invention for the production of 2-vinyl pyridine from a 2-(β-substituted ethyl)-pyridine involves using, as the starting material, a 2-(β-aminoethyl)-pyridine having the formula set out below. The 2-(β-aminoethyl)-pyridine is split by the action of a carrier-bound alkali hydroxide, as a catalyst, at a temperature between 100° and 500° C. into 2-vinyl pyridine and the corresponding secondary amine. Although a certain analogy exists between this dissociation reaction and the production of 2-vinyl pyridine from 2-(β-hydroxyethyl)-pyridine, still the result of this invention could not have been foreseen since only the addition of amines to the C═C double bond of vinyl pyridines to β-aminoethyl pyridines is known from the literature.

The 2-(β-aminoethyl)-pyridine used in the process of this invention have the formula:

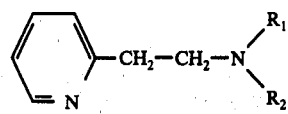

wherein $R_1$ is the same as or different from $R_2$, $R_1$ and $R_2$ each are alkyl having one to eight carbon atoms, cycloalkyl, wherein the alkyl moiety has three to eight carbon atoms, or aralkyl, wherein the alkyl moiety has one to eight carbon atoms, or $R_1$ and $R_2$ together are $-(CH_2)_n-$ wherein $n$ is 4 or 5, or $R_1$ and $R_2$ together are $-(CH_2)_2-O-(CH_2)_2$. Preferably the 2-(β aminoethyl)-pyridine is one which dissociates into a secondary amine which has a great difference of boiling point with regard to 2-vinyl pyridine so that easy separation is possible. Preferred 2-(β-aminoethyl)-pyridines are 2-(β dimethylaminoethyl)-pyridine, 2-(β-diethylaminoethyl)-pyridine and 2-(β-piperidinoethyl)-pyridine.

The 2-(β-aminoethyl)-pyridines used in this invention are easily accessible (i.e., readily producible) in good yields from acetylene and β-aminopropionitriles - this route for production of the starting compound is well known (see Swiss patent application No. 12139/75 of Sept. 18, 1975. β-aminopropionitriles in turn can easily be produced from acrylonitrile and the corresponding secondary amines.

The catalyst of this invention is a dried alkalihydroxide, precipitated on an inert carrier from aqueous solution, for example, sodium or potassium hydroxide on aluminum hydroxide. Other inert carriers include silica gel, kieselguhr, asbestos, calcined magnesium sulfate and diatomaceous earth.

For the production of 2-vinyl pyridine from one of the 2-(β-aminoethyl)-pyridines of this invention, the aminoethyl-pyridine in a gaseous state is conducted continuously through the reactor as a result of which, when using a suitable tarry time, is a conversion of more than 95 percent of the educt and a high reaction selectivity.

Preferably the reaction of this invention is conducted at a temperature between 250° and 450° C.

It is advantageous to carry out the process at a reduced pressure, i.e., at 0.01 to 250 torr and preferably at 1 to 25 torr. The process can be conducted using an installation which basically consists of a dosing arrangement (apparatus), heater, reactor and condensor parts, as well as a suction arrangement (apparatus) following it. The preheating and condensor parts may be varied within wide limits; the reactor part can utilize a solid bed or a turbulent (fluidized) bed.

The raw product consisting of the pertinent secondary amine, 2-vinyl pyridine and a small quantity of unreacted starting material can be separated into components by distillation under reduced pressure, whereby the distillation may be carried out in a separate part of the installation or directly following the reaction. In order to simplify the distillation, it is advantageous to use as a starting product for the reaction those aminoethyl pyridines which result in 2-vinyl pyridine and an amine whose boiling point clearly differs from that of 2-vinyl pyridine.

The process for the production of 2-vinyl pyridine from 2-(β-aminoethyl)-pyridine is suitable for integration into a process of larger scope, whereby acrylonitrile is reacted in succession with a secondary amine and acetylene via aminopropionitrile and 2-(β-aminoethyl)-pyridine into 2-vinyl pyridine and the secondary amine. From this, upon recycle of the secondary amine to the start of the process, a new exceedingly economical process for the production of 2-vinyl pyridine from acrylonitrile and acetylene results.

DETAILED DESCRIPTION OF THIS INVENTION

Example of alkyl groups having one to eight carbon atoms, as used herein, are methyl, ethyl, 1-pentyl, 2-methyl-1-butyl, 3-methyl-1-butyl, 2-methyl-1-pentyl, 3-methyl-1-pentyl, 2-ethyl-1-butyl, 1-propyl, isopropyl, 1-butyl, isobutyl, 2-butyl, 2-pentyl, 3-pentyl, 3-methyl-2-butyl, 2,4-dimethyl-1-pentyl, 1-hexyl, isohexyl, 2-hexyl, 3-hexyl, 2,3-dimethyl-1-butyl, 3-methyl-2-pentyl, 4-methyl-2-pentyl, n-heptyl, 1-octyl and 2-octyl.

Examples of cycloalkyl groups having three to eight carbon atoms, as used herein are cyclohexane, cyclopropane, cyclobutane, cyclopentane, cyclohexane and cyclooctane.

Examples of aralkyl groups, wherein the alkyl moiety therein has one to eight carbon atoms, as used herein, are benzyl, $C_6H_5C_2H_4-$, $C_6H_5C_5H_{10}$, $C_6H_5C_7H_{14}$ and 1-naphthylmethyl.

EXAMPLE 1

A mixture of 150 gm. of annealed $Al_2O_3$ granulate (pellet-shaped, 4 to 5 mm diameter, for example, Spheralite SCS 9 of Rhone Poulenc) and of a solution of 50 gm. of KOH in 85 ml of water is again made anhydrous by distillation and drying at 100° to 300° C. The dried mixture is placed into a reaction tube made of glass (length: 30 cm, diamter: 3 cm). The tube has been provided with an electric jacket heater, as well as a measuring place for the temperature, and is connected by way of its lower end perpendicularly with a 250 ml three-necked flask which is heatable from the outside. Also, on the flask there is a drip funnel and a temperature adapter with thermoelement reaching into the middle of the flask. The upper end of the reaction tube is connected with a receiver (cooled to −78° C.) by way of a short tube bridge to which a manometer is laterally connected. Behind this receiver, and following a further receiver cooled to even deeper temperatures, there is a vacuum pump (as a safety cooling trap), with which constant inside pressures between 0.1 and 230 torr can be produced. This apparatus is evacuated to 20 torr, and the reaction tube and flask (preheater) are heated to 380° C. and 200° C., respectively. Within 45 minutes, 9.2 gm. of 2-(β-diethylaminoethyl)-pyridine is added uniformly via the drip funnel. 9.0 gm. of a condensate which contains 32.9 percent of diethylamine, 55.6 percent of 2-vinyl pyridine and 0.3 percent of 2-(β-diethylaminoethyl)-pyridine is obtained in the receiver. This corresponds to a conversion of 99.7 percent of diethylaminoethyl pyridine and a yield of 92.3 percent of 2-vinyl pyridine.

EXAMPLE 2

In the manner described in Example 1, 9.2 gm. of a mixture of 28.1 percent of diethylamine, 58.9 percent of 2-vinyl pyridine and 0.2 percent of the starting compound is obtained from 9.3 gm. of 2-(β-diethylaminoethyl)-pyridine at 0.1 torr and temperatures of 375° and 170° C. in the reactor and preheater, respectively, at a drip-in time of 90 minutes. This corresponds to a conversion of 99.8 percent and a yield of 98.8 percent of 2-vinyl pyridine.

EXAMPLE 3

Analogously to Example 1, 9.7 gm. of a mixture with 40.4 percent of piperidine, 52.8 percent of 2-vinyl pyridine and 4.7 percent of the starting compound is obtained from 9.8 gm. of 2-(β-piperidinoethyl)-pyridine at 21 torr and 340° C. in the preheater and 360° C. in the reactor with a drip-in time of 120 minutes. This corresponds to a conversion of 95.3 percent and a yield of 94.6 percent of 2-vinyl pyridine.

EXAMPLE 4

As in Example 1, 9.2 gm. of a mixture of 24.2 percent of dimethylamine, 61.7 percent of 2-vinyl pyridine and 2.7 percent of the starting compound is obtained from 9.5 gm. of 2-(β-dimethylaminoethyl)-pyridine at 17 torr and temperatures in the preheater of 200° C. and in the reactor of 360° C. at a drip-in time of 120 minutes. This corresponds to a conversion of 97.4 percent and a yield of 85.5 percent of 2-vinyl pyridine.

EXAMPLE 5

92.5 gm. of a mixture with 33.7 percent of diethylamine, 56.4 percent of 2-vinyl pyridine and 1.1 percent of 2-(β-diethylaminoethyl)-pyridine was obtained in the arrangement described in Example 1 from 93 gm. of 2-(β-diethylaminoethyl)-pyridine at 20 torr and temperatures of 250° C. and 380° C. in the preheater and reactor, respectively, with a drip-in time of 4 hours. The mixture was distilled at 20 torr in a filler column. After a first running with diethylamine as the main component, 48.8 gm. of 2 vinyl pyridine (having a purity of 98.6 percent) was obtained. This corresponds to a yield of 87.7 percent of 2-vinyl pyridine, related to the 2-(β diethylaminoethyl)-pyridine used.

What is claimed is:

1. Process for the production of 2-vinyl pyridine from a 2-(β-substituted ethyl)-pyridine characterized in that a 2-(β-aminoethyl)-pyridine having the formula:

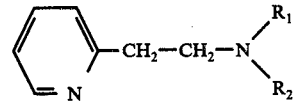

wherein $R_1$ is the same as or different from $R_2$, and $R_1$ and $R_2$ each are alkyl having one to eight carbon atoms, cycloalkyl, wherein the alkyl moiety has three to eight carbon atoms, or aralkyl, wherein the alkyl moiety has one to eight carbon atoms, or $R_1$ and $R_2$ together are a $-(CH_2)_n-$ group, wherein $n$ is 4 or 5, or $R_1$ and $R_2$ together are $-(CH_2)_2-O-(CH_2)_2$, is split through the action of a carrier-bound alkalihydroxide, as a catalyst, at a temperature between 100° and 500° C. into 2-vinyl pyridine and the corresponding secondary amine.

2. Process as claimed in claim 1 wherein the dissociation reaction is carried out at a temperature between 250° and 450° C.

3. Process as claimed in claim 1 wherein a 2-(β-aminoethyl)-pyridine is used which leads to 2-vinyl pyridine and an amine, the boiling point of the amine clearly differing from that of 2-vinyl pyridine.

4. Process as claimed in claim 1 wherein the 2-(β-substituted ethyl)-pyridine is 2-(β-dimethylaminoethyl)- pyridine, 2-(β-diethylaminoethyl)-pyridine or 2-(β-piperidinoethyl)-pyridine.

5. Process as claimed in claim 1 wherein the catalyst is dried sodium or potassium hydroxide, precipitated on aluminum hydroxide from an aqueous solution.

6. Process as claimed in claim 1 wherin the dissociation reaction is carried out at a pressure of 0.01 to 250 torr.

7. Process as claimed in claim 1 wherein the dissociation reaction is carried out at a pressure of 1 to 25 torr.

8. Process as claimed in claim 1 wherein acrylonitrile and the corresponding secondary amine are reacted to produce β-aminoproprionitrile and the β-aminopropionitrile is reacted with acetylene to produce the starting 2-(β-dimethylaminoethyl)-pyridine.

* * * * *